United States Patent [19]

Wachman et al.

[11] Patent Number: 4,923,899

[45] Date of Patent: May 8, 1990

[54] STERILANT COMPOSITION

[75] Inventors: Stanley L. Wachman, Cherry Hill; Sidney Karlan, Nutley, both of N.J.

[73] Assignee: Cetylite Industries, Inc., Pennsauken, N.J.

[21] Appl. No.: 210,626

[22] Filed: Jun. 23, 1988

Related U.S. Application Data

[63] Continuation-in-part of Ser. No. 139,166, Dec. 22, 1987, abandoned, which is a continuation of Ser. No. 906,557, Sep. 8, 1986, abandoned, which is a continuation of Ser. No. 776,479, Sep. 16, 1985, abandoned, which is a continuation-in-part of Ser. No. 692,776, Jan. 18, 1985, abandoned.

[51] Int. Cl.$^5$ .................... A01N 33/12; A01N 35/00
[52] U.S. Cl. .................................. 514/642; 514/643; 514/705
[58] Field of Search .................. 514/642, 643, 705

[56] References Cited

U.S. PATENT DOCUMENTS

| | | | |
|---|---|---|---|
| 3,016,328 | 11/1962 | Pepper et al. | 424/127 |
| 3,282,775 | 11/1966 | Stonehill | 514/705 |
| 4,103,001 | 7/1978 | Schattner | 424/148 |
| 4,107,312 | 8/1978 | Wegner et al. | 424/76 |
| 4,320,147 | 3/1982 | Schaeufele | 514/643 |
| 4,444,785 | 4/1984 | Mandt et al. | 514/496 |

FOREIGN PATENT DOCUMENTS

| | | |
|---|---|---|
| 2145444 | 2/1973 | France . |
| 2321300 | 8/1975 | France . |
| 1443786 | 7/1986 | United Kingdom . |

OTHER PUBLICATIONS

Letartre, C. A., vol. 86 (1977) 86:154.267e.
Borick et al., Journal Pharmaceutical Science, vol. 53, No. 10, pp. 1273-1275.
Oshchepkova et al., C. A. vol. 91 (1979) 91:69799p.
Letartre, C. A. vol. 95 (1981) 95:185,759q.

*Primary Examiner*—Allen J. Robinson
*Attorney, Agent, or Firm*—Lackenbach Siegel Marzullo & Aronson

[57] ABSTRACT

A novel, biocidal, aqueous composition for killing bacteria, spores, fungi, and viruses on nonabsorbent surfaces comprises at least one quaternary ammonium salt, at least one aliphatic dialdehyde having from two to six carbon atoms, and at least one aliphatic hydroxyl compound having from one to eight atoms.

Optionally, a chelating agent and an inorganic nitrite salt may be employed. This sterilant kills bacteria, spores, fungi, and viruses over a pH range from about pH 4 to about pH 9.

2 Claims, No Drawings

STERILANT COMPOSITION

This application is a continuation-in-part of application Ser. No. 139,166 filed Dec. 22, 1987, now abandoned which is a continuation of application Ser. No. 906,557, filed Sept. 8, 1986, now abandoned which is a continuation of application Ser. No. 776 479 filed Sept. 16, 1985, now abandoned which is continuation-in-part of application Ser. No. 692,776 filed Jan. 18, 1985, now abandoned.

BACKGROUND OF THE INVENTION

1. Field of the Invention:

This invention relates to a broad-spectrum biocidal composition effective for rapid killing of bacteria, spores, fungi, and viruses on nonabsorbent surfaces such as dialysis machine tubing, anesthetic breathing bags, surgical instruments, dental bite blocks, saliva draining-tubes, respirator equipment and environmental surfaces in general.

2. Prior Art:

In medical and dental circles, steam sterilization or treatment with ethylene oxide in a closed apparatus have been considered ideal ways of sterilizing equipment. But for many types of parts or apparatus, steam sterilization is impractical because of the size or number of items to be sterilized. For parts of equipment which actually come in contact with the patient, such as dental bite blocks, anesthetic breathing bags, respirators, etc., it is impermissible for ethylene oxide to be used because residual trace amounts might harm the patient.

Hence, a stable, benign, broad-spectrum sterilant effective at a wide range of pHs is greatly desired by the medical/dental profession for environmental use, especially on nonabsorbent surfaces.

A disinfectant is generally considered to be an agent which destroys bacterial organisms which are growing, but not bacterial spores. Germicide and bactericide are approximately synonymous with disinfectant. An antiseptic inhibits the growth of microorganisms. A sporicide kills spores of fungi molds, and bacteria. Since spores are more resistant than bacteria, sporicides are generally considered sterilizing agents. Biocides kill all living microorganisms, hence also are sterilizing agents. A virucide kills viruses; a fungicide kills fungi. The novel sterilant of this invention kills bacteria, spores, fungi and viruses. Hence, it may be termed a biocide or a sterilant.

The Hamilton U.S. Pat. No. 3,208,936, discloses combining a broad range of quaternary amines as germicides and foaming agents in recirculation type toilets.

The Halley U.S. Pat. No. 3,785,971, is directed to a waste treatment material for a storage holding tank in which paraformaldehyde and an alkali carbonate or hydroxide are combined.

U.S. Pat. No. 2,998,390, granted Aug. 29, 1961 to Hamilton and U.S. Pat. No. 3,107,216, granted Oct. 15, 1963 to Hamilton, disclose a recirculating toilet fluid which contains a quaternary ammonium salt.

"Quaternary Ammonium Salts as Germicidals. Nonacylated Quaternary Ammonium Salts Derived from Aliphatic Amines," Shelton, R. S. et al., *Journal of the American Chemical Society*, vol. 68, pp. 753–55 (1946), reported that alkyl quaternary ammonium salts have germicidal powers and N-benzyl substitutes do not affect this germicidal activity.

It was reported in Gardner, J. *Disinfection, Sterilization & Preservation*, p. 900, S.S. Block, ed., Lea & Febiger, 2nd edit. (1977) to include chelating agents with phenols and certain quaternary ammonium salts for enhanced activity against gram-negative bacteria.

The Schattner U.S. Pat. No. 4,103,001 discloses an aqueous mixture of phenol, sodium tetraborate, and sodium phenate solution to which is added aqueous glutaraldehyde in order to kill some bacteria and bacterial spores. This mixture cannot be used against fungi or viruses.

The Stonehill U.S. Pat. No. 3,282,775 discloses a mixture of dialdehydes and a cationic surface active agent, plus a lower alcohol, which kills four spore-forming bacteria, but not fungi or viruses.

The Pepper U.S. Pat. No. 3,016,328 discloses that simple dialdehydes plus a lower alkanol to the extent of about 60 to 70% and an alkalinizing agent to yield a pH range of about 8 to 9.5 kill four spore-forming bacteria, two of which are the same as in U.S. Pat. No. 3,282,775.

Borick, et al in the Journal of Pharmaceutical Sciences, Vol. 53, No. 10 at p. 1273 disclose that glutaraldehyde alkalinized with sodium bicarbonate kills eight nonspore forming bacteria, four sporeforming bacteria, one fungus, and nine viruses, but that this alkaline solution was stable only for about two weeks.

French Patent No. 2,321,300 discloses that a mixture of aldehyde and quaternary ammonium compound has antiseptic properties by reducing the growth of five bacteria of interest to the food industry.

British Patent No. 1,443,786 discloses that a mixture of glutaraldehyde, a lower alcohol, and a highly ionizable salt at acidic pH ranges kills four sporulating bacteria by ion exchange with the calcium in the walls of the bacterial spores.

The Wagner U.S. Pat. No. 4,107,312 discloses a disinfectant mixture of a strong formaldehyde solution, plus minor amounts of glyoxal and glutaraldehyde, plus a quaternary ammonium salt, methanol to stabilize the formaldehyde, a nonionic wetting agent, optionally some alcohol or glycol, and a scent, all at a neutral pH in order to avoid corrosion of aluminum toilets (or minimize corrosion of magnesium toilets) in aircraft.

The Mandt U.S. Pat. No. 4,444,785 discloses a disinfecting solution for soft contact lenses against two nonsporulating bacteria comprising a very low concentration of 1,5 pentanedial at neutral pH compatible with the human eye.

The Schaeufele U.S. Pat. No. 4,320,147 discloses a germicidal composition comprising quaternary ammonium chlorides, plus builder salts, which are useful for disinfection against bacteria.

Canadian Patent No. 1,154,555 discloses a bacteriocide composition containing formaldehyde, glutaraldehyde and a quaternary ammonium ingredient.

French Patent No. 2,145,444 discloses a bacteriocide composition containing formaldehyde and a quaternary ammonium compound.

The Lockwood U.S. Pat. No. 3,505,690 relates to a disinfectant dispersing system.

The Buchalter U.S. Pat. No. 3,983,252 discloses a chemical disinfecting composition comprising a dialdehyde and an alkali metal salt of a hydrocarbon carboxylic acid and optionally an alcohol.

The Goldhaft U.S. Pat. No. 4,022,911 discloses a disinfectant composition comprising three essential active ingredients, namely a dimethyl quaternary ammonium halogen salt, a phenol or derivative thereof, and formaldehyde.

OBJECTS OF THE INVENTION

It is an object of this invention to provide a stable, benign, nonodorous, solution which kills a broad spectrum of bacteria, spores, fungi, and viruses rapidly at a wide range of pH.

It is a further object of this invention to provide a broad-spectrum sterilant which will remain an active solution for at least several weeks.

It is yet another object of this invention to provide a sterilant which is effective on hard, nonabsorbent, "environmental" surfaces such as anesthetic breathing bags, dialysis tubing, respirators, dental bite blocks, saliva-draining tubes, and the like for which sterilization by steam or ethylene oxide is either impractical or physiologically disfavored.

It is an object of the present invention to provide a sterilant composition effective for killing rapidly individual microorganisms or a combination of several different kinds of microorganisms, such as bacteria, spores, fungi and/or viruses.

Other objects of the present invention will be apparent to those skilled in the art.

SUMMARY OF THE INVENTION

Surprisingly, a broad-spectrum sterilant capable of rapidly killing bacteria, sporulating bacteria, spores, fungi, and viruses can be achieved by combining in an aqueous solution an effective amount of at least one quaternary ammonium compound, at least one aliphatic dialdehyde having from two to six carbon atoms, and at least one aliphatic hydroxyl compound having from one to eight carbon atoms.

Another aspect of the invention relates to the use of the novel sterilant on "hard" or "environmental" surfaces (nonabsorbing) such as medical or dental equipment for which previously steam sterilization or treatment with ethylene oxide were employed.

The sterilant of the present invention relates to a liquid composition which is effective for rapidly killing at least one microorganism or any combination of two or more different microorganisms such as bacteria, spores, fungi and viruses.

For still another aspect of the invention, the novel sterilant is employed over a wide range of pH and is stable for several weeks after having been compounded.

A typical embodiment of the invention comprises:

| Component | Weight % |
|---|---|
| Alkylbenzyldimethylammonium chloride | 0.1 |
| Cetyldimethylethylammonium bromide | 0.1 |
| Glutaraldehyde | 2.6 |
| Isopropyl alcohol | 0.2 |
| Propylene glycol | 0.16 |
| Sodium nitrite | 0.11 |
| Tetrasodium ethylenediamine tetracetate | 0.015 |
| Water | balance |

Processes for employing these sterilant compositions ar also disclosed herein.

DETAILED DESCRIPTION OF PREFERRED EMBODIMENTS

Quaternary ammonium salts in aqueous solution are known to kill simple, nonsporulating, Gram-positive, and Gram-negative bacteria such as *Staphylococcus aureus, Salmonella choleraesuis,* Pseudonomas *aeruginosa, Escherichia coli,* and the like within 10 minutes or less. More difficult to kill are spore-forming, or sporulating, bacteria such as *Bacillus globigii, Bacillus subtilis, clostridium tetani, C. perfringens, C. Sporogenes,* etc. This can be carried out by alkalinized dialdehydes at comparatively high concentration and high pH, but alkalinized solutions of aldehydes are unstable because of potential condensation and redox reactions.

Chemical agents for killing fungi such as *Trichophyton interdigitale,* and *T. mentagrophytes* and viruses such as Coxsackie B-1, Herpes Simplex I, Influenza A, Adeno type II and the like are known, but hitherto it has not been clear what types of chemicals or mixtures of chemicals kill all the above forms of microorganisms at a broad range of pH on "hard" surfaces and thus render the surfaces sterile.

The cationic, quaternary salts useful in the present invention may contain either or both of aliphatic and aromatic moieties. Although quaternary ammonium salts are preferred, cationic phosphonium, or positive sulfur, or any other positive non-metallic nuclei may be selected. Some of the aliphatic or alicyclic substituents for the quaternary ions are alkyl groups containing one to 30 carbon atoms both linear and branched, alkoxy groups also containing one to 30 carbon atoms both linear and branched, alicylic groups such as cyclohexyl and its alkylated or alkyloxylated derivatives, and halogenated alkyl, halogenated alicyclic, or halogenated alkyloxy derivatives.

Aromatic moieties, which may themselves be substituted by aliphatic, alicyclic, alkyloxy groups, useful as substituents for the quaternary cationic salts of the present invention are benzyl, tolyl, xylyl, naphthyl, pyridyl, benzal, quinolyl and the like.

The preferred counterions for the quaternary cationic salts are halides, especially chloride and bromide. Particularly useful for practicing the present invention are alkylbenzyldimethylammonium chlorides, wherein the alkyl groups contain between 10 and 18 carbon atoms, and cetyldimethylethylammonium bromide. The useful range of quaternary cationic salts in an effective amount of sterilant is from about 0.05% to 3% in actual use by weight.

The solubility of the various solutes in the novel sterilant of the instant invention is improved by using small amounts of alkanols having from one to six carbon atoms and/or glycols having from two to four carbon atoms. These alkanols and glycols also have concomitant and peripheral biocidal effect. Especially useful alkanols are methanol, ethanol, and isopropyl alcohol. Especially useful polyols are glycols such as ethylene glycol, propylene glycol, diethylene glycol, as well as glycerine. In the diluted solution for actual use, the effective amount for the alkanol is from about 0.1% to 3% by weight, and the effective amount for the polyol or glycol is from about 0.1% to 3% by weight.

Certain salts with anions at less than full oxidation state, such as nitrite, bisulfite, or chlorite, may be optionally employed in the novel sterilant solution of the instant invention to prevent corrosion, as well as for their biocidal activity. Particularly useful are sodium, potassium, lithium, and ammonium salts of the three anions named; especially useful is sodium nitrite. These optional salts may be employed in the range from 0.05% to about 2.0% by weight of the actual solution employed.

A chelating agent may be optionally employed in the broad-spectrum sterilant of the present invention from 0% to 0.025% by weight to aid in solubility of the other components, to counteract any deleterious effects from diluting concentrated commercial strengths with hard water for use, and to help break down the coatings of spores, which have a high concentration of multivalent ions. The preferred chelating agent to practice the current invention may range from 0% to 0.025% by weight and is ethylene diamine tetraacetic acid (EDTA). Partial esters or salts of EDTA may also be used. An example of a salt of EDTA is tetrasodium ethylenediamine tetraacetate.

The aliphatic dialdehyde containing from two to six carbon atoms is a component of the broad-spectrum sterilant of the present invention. Dialdehydes include malonaldehyde, succinaldehyde, oxaldehyde (glyoxal), adipaldehyde, and preferably glutaraldehyde. Alternatively, these compounds may be termed aliphatic dials, e.g. 1, 5 pentanedial. By themselves, these compounds are effective germicides to some degree, at high pH, but they fail to have the wide breadth and speed of killing of the mixture of the current invention. This is especially true for the killing of the sporulent bacteria, where the dialdehydes alone can take up to ten hours to kill spores, and for many viruses, where dialdehydes are ineffective. In the final dilution as used, in the present invention, an effective amount of the dialdehyde is from about 0.5% to about 7% by weight. A concentration of dialdehyde of about 2.6 weight % is preferred and a concentration of dialdehyde of 3.2 weight % is especially preferred.

As a practical matter, it is preferred to produce the broad-spectrum sterilant of the present invention in the form of one or more concentrated solutions prior to transport and storage. The concentrations of these solutions would be 50 to 100-fold higher strength than the actual use-strengths given above. After transport and storage, the user, normally a medical or dental technician, will dilute the concentrate to produce an effective amount at the ultimate dilution.

In concentrated form, a preferred embodiment of the sterilant concentrate of the present invention would have the following approximate concentrations by weight:

|  | Wt. % |
| --- | --- |
| Alkyl*benzyldimethylammonium chloride | 7 |
| *50% C-12, 30% C-14, 17% C-16, 3% C-18 | |
| Cetyldimethylethylammonium bromide | 7 |
| Isopropyl Alcohol | 14 |
| Propylene glycol | 12 |
| Sodium nitrite | 7 |
| EDTA | 1.5 |
| Water, balance up to 100% | |

In actual practice, the user will have prepared a desired quantity of the diluted sterilant concentrate by diluting the sterilant concentrate with distilled or tap water. This resulting solution will serve, further, as the diluent for the dialdehyde concentrate then to be added thereto.

The present invention will now be described by reference to the following examples, which are not to be deemed limitative of the present invention in any manner thereof.

EXAMPLE A

This example illustrates the preparation of an effective sterilizing amount of a final user solution of the sterilant composition of the invention.

A 15 ml ampule of the above sterilant concentrate was diluted with distilled water to a final volume of 1 liter. This was a dilution ratio of about 66.7:1. To this solution was added 50 ml of an aqueous 50% by weight solution of glutaraldehyde concentrate. On a weight basis, the concentration of glutaraldehyde will be about 2.6% in the final user solution.

Thus in the final user solution, the concentrations of the various components in the diluted sterilant will be as follows:

|  | Wt. % |
| --- | --- |
| Alkylbenzyldimethylammonium chloride | 0.1 |
| Cetyldimethylethylammonium bromide | 0.1 |
| Isopropyl alcohol | 0.2 |
| Propylene glycol | 0.16 |
| Sodium nitrite | 0.1 |
| EDTA | 0.02 |
| Dialdehyde, esp. glutaraldehyde | 2.6 |
| Water | balance |

The diluted sterilant composition of the present invention may be employed over a wide, useful pH range from about pH 4 to about pH 9. The preferred range for use is from about pH 5 to about pH 8. This is in marked contrast to the use of alkalinized dialdehydes alone, which are effective only from about pH 7 to about pH 8.5. Although buffers may optionally be employed to keep the sterilant of the instant invention within a narrow pH range, no buffer is necessary to practice this invention.

EXAMPLE B

This example illustrates the preparation of an effective sterilizing amount of a final user solution of the sterilant composition of the invention.

A 15 ml ampule of the above sterilant concentrate was diluted with distilled water to a final volume of 750 ml. This was a dilution ratio of about 50:1. To this solution was added 50 ml of an aqueous 50% by weight solution of glutaraldehyde concentrate. On a weight basis, the concentration of glutaraldehyde will be about 3.2% in the final user solution.

Thus, in the final user solution, the concentrations of the various components in the diluted sterilant will be as follows:

|  | Wt. % |
| --- | --- |
| Alkylbenzyldimethylammonium chloride | 0.15 |
| Cetyldimethylethylammonium bromide | 0.15 |
| Isopropyl alcohol | 0.25 |
| Propylene glycol | 0.20 |
| Sodium nitrite | 0.15 |
| EDTA | 0.025 |
| Dialdehyde, esp. glutaraldehyde | 3.2 |
| Water | balance |

The diluted sterilant composition of the present invention may be employed over a wide, useful pH range from about pH 4 to about pH 9. The preferred range for use is from about pH 5 to about pH 8. This is in marked contrast to the use of alkalinized dialdehydes alone, which are effective only from about pH 7 to about pH 8.5. Although buffers may optionally be employed to keep the sterilant of the instant invention within a narrow pH range, no buffer is necessary to practice this invention.

EXAMPLE 1

This example illustrates the effectiveness of the sterilant composition of EXAMPLE A for nonsporulating bacteria.

The novel sterilant of the present invention was prepared with 400 ppm hard water as the diluent for test purposes:

|  | Wt. % |
|---|---|
| Alkylbenzyldimethylammonium chloride | 0.1 |
| Cetyldimethylethylammonium bromide | 0.1 |
| Isopropyl alcohol | 0.2 |
| Propylene glycol | 0.16 |
| Sodium nitrite | 0.11 |
| EDTA | 0.02 |
| Glutaraldehyde | 2.60 |
| Water | balance |

Employing the Use-Dilution Method of the Association of Official Agricultural Chemists (AOAC) 60 ring carriers were tested on three batchs each for efficacy against the following organisms (US EPA Procedure DIS/TSS-1 and 2 of Jan. 1982); *Salmonella choleraesius* ATCC 10708 (Gram-negative), *Staphylococcus aureus* ATCC 6538 (Gram-positive), and *Pseudomonas aeruginosa* ATCC 15442 (Gram-positive, nosocomial pathogen).

All these microorganisms were killed within 10 minutes at 20 degrees C.

EXAMPLE 2

This example illustrates the efficacy of the broadspectrum sterilant of the present invention for killing sporulating bacteria.

The novel sterilant solution was prepared as in EXAMPLE 1 for testing against Gram-positive, sporulating bacteria *Bacillus subtilus* ATCC 19659 and *Clostridium sporogenes* ATCC 3584 employing US EPA Procedure DIS/TSS-9 of April 1981 (AOAC Sporicidal Test). Sixty carriers for each type of surface, porcelain penicylinders and silk suture loops, for each of three samples for each of three batches involved a total of 720 carriers.

As required, all microorganisms were killed on all carriers in about 5 hours, less than 6 hours at 20 degrees C.

In a similar test alkalinized glutaraldehyde can meet this standard only after 10 hours of contact.

EXAMPLE 3

This example illustrates the efficacy of the broadspectrum sterilant of the present invention for killing fungi and fungal spores.

The novel sterilant solution was prepared as in EXAMPLE 1 for testing against pathogenic fungus *Trichophyton mentagrophytes* ATCC 27289 according to the AOAC Fungicidal Test by EPA procedure DIS/TSS-6 of August 1981. For this fungus two batches were used for two samples each killing all organisms within 10 minutes at 20 degrees C.

EXAMPLE 4

This example illustrates the efficacy of the broadspectrum sterilant of the present invention in killing viruses, some of which none of the components of the novel sterilant can kill individually under the same conditions.

The novel sterilant solution was prepared as in EXAMPLE 1 for testing against the following viruses: Herpes Simplex I and II, Coxsackie virus B1, Coxsackie virus A9, Vaccinia Virus, Influenza virus A, Adenos virus II, Poliovirus I, Rhino virus, Cytomegalo virus, and Corona virus, all according to EPA procedure DIS/TSSD-7. For two batches each, four replicates were carried by ten-fold dilution and measured to three-log diminution. After incubation, the samples were recovered after adsorption time on mammalian cell monolayers.

The novel sterilant inactivated all the viruses within 10 minutes at 20 degrees C. It is known that alkalinized glutaraldehyde fails to inactivate at least Coxsackie virus and Poliovirus I under these conditions.

EXAMPLE 5

This example illustrates the effectiveness of the sterilant composition of EXAMPLE B for nonsporulating bacteria.

The novel sterilant of the present invention was prepared with 400 ppm hard water as the diluent for test purposes:

|  | Wt. % |
|---|---|
| Alkylbenzyldimethylammonium chloride | 0.15 |
| Cetyldimethylethylammonium bromide | 0.15 |
| Isopropyl alcohol | 0.25 |
| Propylene glycol | 0.20 |
| Sodium nitrite | 0.15 |
| EDTA | 0.025 |
| Glutaraldehyde | 3.2 |
| Water | balance |

Employing the Use-Dilution Method of the Association of Official Agricultural Chemists (AOAC) 60 ring carriers were tested on three batchs each for efficacy against the following organisms (US EPA Procedure DIS/TSS-1 and 2 of January 1982); *Salmonella choleraesius* ATCC 10708 (Gram-negative), *Staphylococcus aureus* ATCC 6538 (Gram-positive), and *Pseudomonas aeruginosa* ATCC 15442 (Gram-positive, nosocomial pathogen). All these microorganisms were killed within 10 minutes at 20 degrees C.

EXAMPLE 6

This example illustrates the efficacy of the broadspectrum sterilant of the present invention for killing sporulating bacteria.

The novel sterilant solution was prepared as in EXAMPLE 5 for testing against Gram-positive, sporulating bacteria *Bacillus subtilus* ATCC 19659 and *Clostridium sporogenes* ATCC 3584 employing US EPA Procedure DIS/TSS-9 of April 1981 (AOAC Sporicidal Test). Sixty carriers for each type of surface, porcelain penicylinders and silk suture loops, for each of three samples for each of three batches involved a total of 720 carriers.

As required, all microorganisms were killed on all carriers in about 5 hours, less than 6 hours at 20 degrees C.

In a similar test alkalinized glutaraldehyde can meet this standard only after 10 hours of contact.

EXAMPLE 7

This example illustrates the efficacy of the broadspectrum sterilant of the present invention for killing fungi and fungal spores.

The novel sterilant solution was prepared as in EXAMPLE 5 for testing against pathogenic fungus Trichophyton mentagrophytes ATCC 27289 according to the AOAC Fungicidal Test by EPA procedure DIS/TSS-6 of August 1981. For this fungus two batches were used for two samples each killing all organisms within 10 minutes at 20 degrees C.

EXAMPLE 8

This example illustrates the efficacy of the broadspectrum sterilant of the present invention in killing viruses, some of which none of the components of the novel sterilant can kill individually under the same conditions.

The novel sterilant solution was prepared as in EXAMPLE 5 for testing against the following viruses: Herpes Simplex I and II, Coxsackie virus B1, Coxsackie virus A9, Vaccinia Virus, Influenza virus A, Adenos virus II, Poliovirus I, Rhino virus, Cytomegalo virus, and Corona virus, all according to EPA procedure DIS/TSSD-7. For two batches each, four replicates were carried by ten-fold dilution and measured to three-log diminution. After incubation, the samples were recovered after adsorption time on mammalian cell monolayers.

The novel sterilant inactivated all the viruses within 10 minutes at 20 degrees C. It is known that alkalinized glutaraldehyde fails to inactivate at least Coxsackie virus and Poliovirus I under these conditions.

The sterilant composition of the present invention has the advantages of being effective to kill a broad spectrum of microorganisms very rapidly with low concentrations of the active ingredients. The sterilant composition as a combination of ingredients is more effective against several microorganisms together at the same time than would be possible by using each active ingredient separately against the combination of microorganisms.

Having illustrated the instant invention with the foregoing Examples, the scope of legal protection sought for this invention is set forth in the claims which follow.

We claim:

1. A sterilant composition for killing on a nonabsorbent surface bacteria, spores, fungi, and viruses selected from the group consisting of *Salmonella Chloreraesuis* (ATCC 10708), *Staphylococcus aureus* (ATCC 19659), *Pseudomonas aeruginosa* (ATCC 15442), *Bacillus subtilis* (ATCC 19659) *Clostridium sporogeneses* (ATCC 3584), *Trichophyton mentagrophytes* (ATCC 27289), Herpes Simplex I, Herpes Simplex II, Coxsackie virus BI, Coxsackie virus A9, Vaccinia virus, Influenza virus A, Adeno virus II, Poliovirus I, Rhino virus, Cytomegalo virus, and Corona virus, consisting of (a) from about 0.05 wgt % to about 3 wgt % of alkylbenzyldimethyl ammonium chloride wherein the alkyl group has from 10 to 18 carbon atoms,
   (b) from about 0.5 wgt % to about 7 wgt % of glutaraldehyde,
   (c) from about 0.05 wgt % to about 3 wgt % of cetyldimethylethylammonium bromide,
   (d) from about 0.1 wgt % to about 3 wgt % of an alcohol having from one to six carbon atoms,
   (e) from about 0.05 wgt % to about 2 wgt % of a less than totally oxidized salt whose anion is selected from the group consisting of nitrite, bisulfite, and chlorite and who cation is selected from the group consisting of sodium, potassium, lithium and ammonium,
   (f) from about 0.1 wgt % to about 3 wgt % of a polyol selected from the group consisting of ethylene glycol, propylene glycol, diethylene glycol, and glycerine,
   (g) from 0 to 0.015 wgt % of a salt or ester of ethylene diamine tetraacetic acid, and
   (h) balance of water.

2. A method for sterilizing a nonabsorbent surface comprising the steps of contacting said surface with an effective amount of a sterilant composition consisting of:

(a) from about 0.05 wgt % to about 3 wgt % of alkylbenzyldimethyl ammonium chloride wherein the alkyl group has from 10 to 18 carbon atoms,
   (b) from about 0.5 wgt % to about 7 wgt % of glutaraldehyde,
   (c) from about 0.05 wgt % to about 3 wgt % of cetyldimethylethyl ammonium bromide,
   (d) from about 0.1 wgt % to about 3 wgt % of an alcohol having from one to six carbon atoms,
   (e) from about 0.05 wgt % to about 2 wgt % of a less than totally oxidized salt whose anion is selected from the group consisting of nitrite, bisulfite, and chlorite and whose cation is selected from the group consisting of sodium, potassium, lithium and ammonium,
   (f) from about 0.1 wgt % to about 3 wgt % of a polyol selected from the group consisting of ethylene glycol, propylene glycol, diethylene glycol, and glycerine,
   (g) from 0 to 0.015 wgt % of a salt or ester of ethylene diamine tetraacetic acid, and
   (h) the balance of water, and killing on said surface bacteria, spores, fungi, and viruses selected from the group consisting of *Salmonella Choleraesuis* (ATCC 10708), *Staphylococcus aureus* (ATCC 6538), *Pseudomonas aeruginosa* (ATCC 15442), *Bacillus subtilis* (ATCC 19659), *Clostridium sporogeneses* (ATCC 3584), *Trichophyton mentagrophytes* (ATCC 27289), Herpes Simplex I, Herpes Simplex II, Coxsackie virus BI, Coxsackie virus A9, Vaccinia virus, Influenza virus A, Adeno virus II, Poliovirus I, Rhino virus, Cytomegalo virus, and Corona virus.

* * * * *